US010206638B2

United States Patent
Nakai

(10) Patent No.: US 10,206,638 B2
(45) Date of Patent: Feb. 19, 2019

(54) X-RAY CT AND MEDICAL DIAGNOSTIC APPARATUS WITH PHOTON COUNTING DETECTOR

(71) Applicant: Toshiba Medical Systems Corporation, Otawara-shi (JP)

(72) Inventor: Hiroaki Nakai, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 470 days.

(21) Appl. No.: 14/966,164

(22) Filed: Dec. 11, 2015

(65) Prior Publication Data

US 2016/0095560 A1 Apr. 7, 2016

Related U.S. Application Data

(63) Continuation of application No. PCT/JP2014/065483, filed on Jun. 11, 2014.

(30) Foreign Application Priority Data

Jun. 20, 2013 (JP) ................................ 2013-130011

(51) Int. Cl.
*A61B 6/00* (2006.01)
*G01T 1/16* (2006.01)
(Continued)

(52) U.S. Cl.
CPC .......... *A61B 6/4241* (2013.01); *A61B 6/4233* (2013.01); *G01T 1/1603* (2013.01);
(Continued)

(58) Field of Classification Search
CPC ........... A61B 6/00; A61B 6/42; A61B 6/4208; A61B 6/4233; A61B 6/4241; A61B 6/48;
(Continued)

(56) References Cited

U.S. PATENT DOCUMENTS

| 5,151,588 A | 9/1992 | Kiri et al. |
| 7,916,836 B2 | 3/2011 | Tkaczyk et al. |

(Continued)

FOREIGN PATENT DOCUMENTS

| JP | 3-165291 | 7/1991 |
| JP | 8-68864 | 3/1996 |

(Continued)

OTHER PUBLICATIONS

International Search Report dated Sep. 9, 2014 in PCT/JP2014/065483, filed Jun. 11, 2014 (with English Translation).

(Continued)

*Primary Examiner* — Anastasia Midkiff
(74) *Attorney, Agent, or Firm* — Oblon, McClelland, Maier & Neustadt, L.L.P.

(57) ABSTRACT

An X-ray CT apparatus according to an embodiment includes a detector, counted result collecting circuitry, count rate calculating circuitry, control circuitry, and image reconstruction circuitry. The detector includes a plurality of detection elements including a plurality of types of detection elements with different response characteristics to an X-ray dose, and outputs a detection signal according to an incidence of an X-ray photon to each of the detection elements. The counted result collecting circuitry collects counted results obtained by counting X-ray photons from detection signals output by the detection elements. The count rate calculating circuitry calculates a count rate from the detection signals output by the detection elements. The control circuitry selects a detection element based on the count rate and respective response characteristics of the detection elements. The image reconstruction circuitry reconstructs X-ray CT image data using the counted result obtained from the detection element selected by the control circuitry.

10 Claims, 9 Drawing Sheets

(51) Int. Cl.
  *G06T 11/00* (2006.01)
  *A61B 6/03* (2006.01)
  *G01T 1/29* (2006.01)
(52) U.S. Cl.
  CPC ............... *A61B 6/03* (2013.01); *A61B 6/4035* (2013.01); *A61B 6/482* (2013.01); *A61B 6/5205* (2013.01); *A61B 6/54* (2013.01); *A61B 2562/066* (2013.01); *G01T 1/2985* (2013.01); *G06T 11/005* (2013.01); *G06T 2207/10081* (2013.01)
(58) Field of Classification Search
  CPC ......... A61B 6/482; A61B 6/52; A61B 6/5205; A61B 6/5294; A61B 2562/00; A61B 2562/06; A61B 2562/066; A61B 2576/00; G01T 1/00; G01T 1/16; G01T 1/1603; G01T 1/161; G01T 1/24; G01T 1/243; G01T 1/245; G01T 1/246; G01T 1/29; G01T 1/2914; G01T 1/2985; G01T 1/2992; G01T 7/00; G06T 1/00; G06T 1/0007; G06T 1/60; G06T 7/00; G06T 7/0012; G06T 11/00; G06T 11/003; G06T 11/005; G06T 2200/00; G06T 11/28; G06T 2210/41; G06T 2211/00; G06T 2211/40; G06T 2211/408; G06T 2211/412; G06T 2207/00; G06T 2207/10; G06T 2207/10072; G06T 2207/10081; G06T 2207/20; G06T 2207/20004; G06T 2207/20012; G06T 2207/30; G06T 2207/30004

See application file for complete search history.

(56) References Cited

U.S. PATENT DOCUMENTS

| | | | |
|---|---|---|---|
| 2006/0056581 A1* | 3/2006 | Hoffman | A61B 6/032 378/19 |
| 2007/0206721 A1 | 9/2007 | Tkaczyk et al. | |
| 2008/0260094 A1 | 10/2008 | Carmi | |
| 2014/0183371 A1* | 7/2014 | Roessl | G01T 1/241 250/370.09 |
| 2014/0314211 A1* | 10/2014 | Zou | G01T 1/171 378/207 |
| 2015/0063527 A1* | 3/2015 | Daerr | G01T 1/171 378/5 |

FOREIGN PATENT DOCUMENTS

| | | |
|---|---|---|
| JP | 2009-18154 | 1/2009 |
| JP | 2009-78143 | 4/2009 |
| JP | 2009-513220 | 4/2009 |
| JP | 2012-34901 | 2/2012 |
| JP | 2012-187143 | 10/2012 |

OTHER PUBLICATIONS

Written Opinion dated Sep. 9, 2014 in PCT/JP2014/065483, filed Jun. 11, 2014.

* cited by examiner

X-RAY CT AND MEDICAL DIAGNOSTIC APPARATUS WITH PHOTON COUNTING DETECTOR

CROSS-REFERENCE TO RELATED APPLICATIONS

This application is a continuation of PCT international application Ser. No. PCT/JP2014/065483 filed on Jun. 11, 2014 which designates the United States, incorporated herein by reference, and which claims the benefit of priority from Japanese Patent Applications No. 2013-130011, filed on Jun. 20, 2013, incorporated herein by reference.

FIELD

Embodiments described herein relate generally to an X-ray CT apparatus and a medical image diagnostic apparatus.

BACKGROUND

In recent years, the development of X-ray CT apparatus that performs photon counting CT (computed tomography) using a photon counting type detector is progressed. Unlike an integration type detector used in conventional X-ray CT apparatuses, the photon counting type detector can count an incident X-ray photon individually, and outputs a signal capable of measuring (discriminating) energy of the incident X-ray photon.

Each of detection elements constituting the photon counting type detector outputs one signal (response waveform), for example, each time an X-ray photon enters. In photon counting CT, a response waveform output by the detection element is counted. Moreover, in the photon counting CT, the energy of an incident X-ray photon is measured from a signal intensity (height of wave, etc.) of the counted response waveform. This enables the photon counting CT to reconstruct an X-ray CT image with a high S/N (Signal per Noise) ratio, as compared with conventional X-ray CT images.

However, the response waveform takes time for attenuation, and therefore when X-ray photons enter at a high frequency (in high doses), a next photon enters before the signal, which is output by the previously incident photon, attenuates, and response waveforms of a plurality of X-ray photons overlap each other. Such a phenomenon is called "pile up", and once a pile up occurs, the number of X-ray photons and their energy spectra cannot correctly be measured. Moreover, when an X-ray dose to be emitted is decreased so that X-ray photons enter at a low frequency (in low doses) to such an extent that the pile up will not occur, the number of photons counted by the photon counting type detector is reduced when a distance, in which the X-ray passes through a subject, is large, and the S/N ratio of a reconstructed image is degraded and an artifact occurs.

On the other hand, in the photon counting type detector, it is known that there is a detector capable of reducing occurrence of a pile up by providing a plurality of detection elements in an area corresponding to one pixel and adjusting the number of elements used for reconstruction according to an X-ray dose. However, the detector requires microfabrication (½, ⅓, or so) more than twice the detection element, and further requires a circuit for switching the detection elements, which leads to high production cost of the detector.

DETAILED DESCRIPTION

An X-ray CT apparatus according to an embodiment includes a detector, counted result collecting circuitry, count rate calculating circuitry, control circuitry, and image reconstruction circuitry. The detector includes a plurality of detection elements including a plurality of types of detection elements with different response characteristics to an X-ray dose, and outputs a detection signal according to an incidence of an X-ray photon to each of the detection elements. The counted result collecting circuitry collects counted results obtained by counting X-ray photons from detection signals output by the detection elements. The count rate calculating circuitry calculates a count rate from the detection signals output by the detection elements. The control circuitry selects a detection element based on the count rate and respective response characteristics of the detection elements. The image reconstruction circuitry reconstructs X-ray CT image data using the counted result obtained from the detection element selected by the control circuitry.

Exemplary embodiments of the X-ray CT (Computer Tomography) apparatus will be explained in detail below with reference to the accompanying drawings.

The X-ray CT apparatus explained in the following embodiments is a device capable of executing photon counting CT. That is, the X-ray CT apparatus explained in the following embodiments use not the conventional integration type (current mode measurement method) detector but the photon counting type detector for reconstructing X-ray CT image data.

Embodiments

First of all, the photon counting CT will be explained before the X-ray CT apparatus according to a present embodiment is explained.

Each of detection elements constituting the conventional integration type detector outputs a current corresponding to an integrated value of the energy (X-ray intensity) of individual incident X-ray photons. On the other hand, each of detection elements constituting the photon counting type detector outputs a detection signal according to an incidence of an X-ray photon. For example, each of the detection elements constituting the photon counting type detector outputs one detection signal (response waveform) each time an X-ray photon enters. In photon counting CT, a response waveform output from each detection element is counted. Moreover, in the photon counting CT, energy of the incident X-ray photon is measured from a signal intensity (height of wave, etc.) of the counted response waveforms. This makes it possible for the photon counting CT to reconstruct X-ray CT image data with a high S/N ratio. In the photon counting CT, X-ray CT image data for each of a plurality of energy components can be reconstructed. For example, in the photon counting CT, it is possible to obtain image data capable of identifying a substance using the difference between K-absorption edges.

Figure 1:
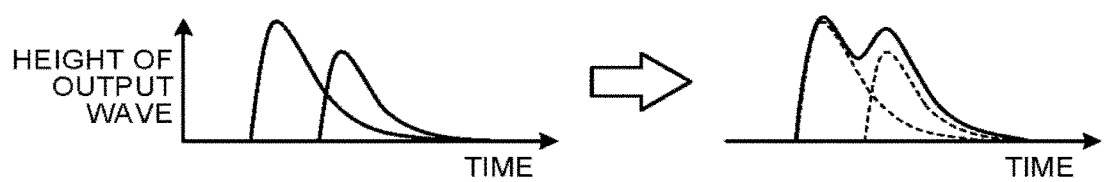
FIG. 1 is a diagram for explaining a pile up.

However, in the photon counting CT, occurrence of a pile up may cause the S/N ratio of the reconstructed image to be degraded and the artifact to occur. FIG. 1 is a diagram for explaining the pile up. The horizontal axis in FIG. 1 indicates the time, and the vertical axis in FIG. 1 indicates the height of wave of a response waveform.

The response waveform takes a time to attenuate, and therefore, when the X-ray photon enters at a high frequency (in high doses), the next photon enters before the signal, which is output by the previously incident photon, attenuates, and response waveforms of a plurality of X-ray photons overlap each other (See the left view of FIG. 1). Such a phenomenon is called "pile up". When a pile up occurs, as illustrated in the right view of FIG. 1, for example, an observed response waveform has a shape in which two response waveforms overlap each other, and individual waveforms cannot be separated from each other. In this way, when the pile up occurs, the number of photons to be counted is reduced more than the number of photons that actually enter the detection element. As illustrated in the right view of FIG. 1, even if the waveform in which the two waveforms overlap due to the pile up is used, the energy of the X-ray photons cannot be correctly measured. Because of this, once the pile up occurs, the S/N ratio of X-ray CT image data may be degraded or the artifact may occur.

Moreover, when an X-ray dose to be emitted is reduced so that X-ray photons enter at a low frequency (in low doses) to such an extent that the pile up will not occur, the number of photons counted by the photon counting type detector is reduced when a distance where the X-ray passes through a subject is large or in similar cases, and therefore the S/N ratio of the reconstructed image is degraded and the artifact occurs.

On the other hand, in the photon counting type detector, it is known that there is a detector capable of reducing occurrence of a pile up by providing a plurality of detection elements in an area corresponding to one pixel and adjusting the number of elements used for reconstruction according to the X-ray dose. However, the detector requires microfabrication (½, ⅓, or so) more than twice the detection element, and further requires a circuit for switching the detection elements, which leads to high production cost of the detector.

Figure 2:
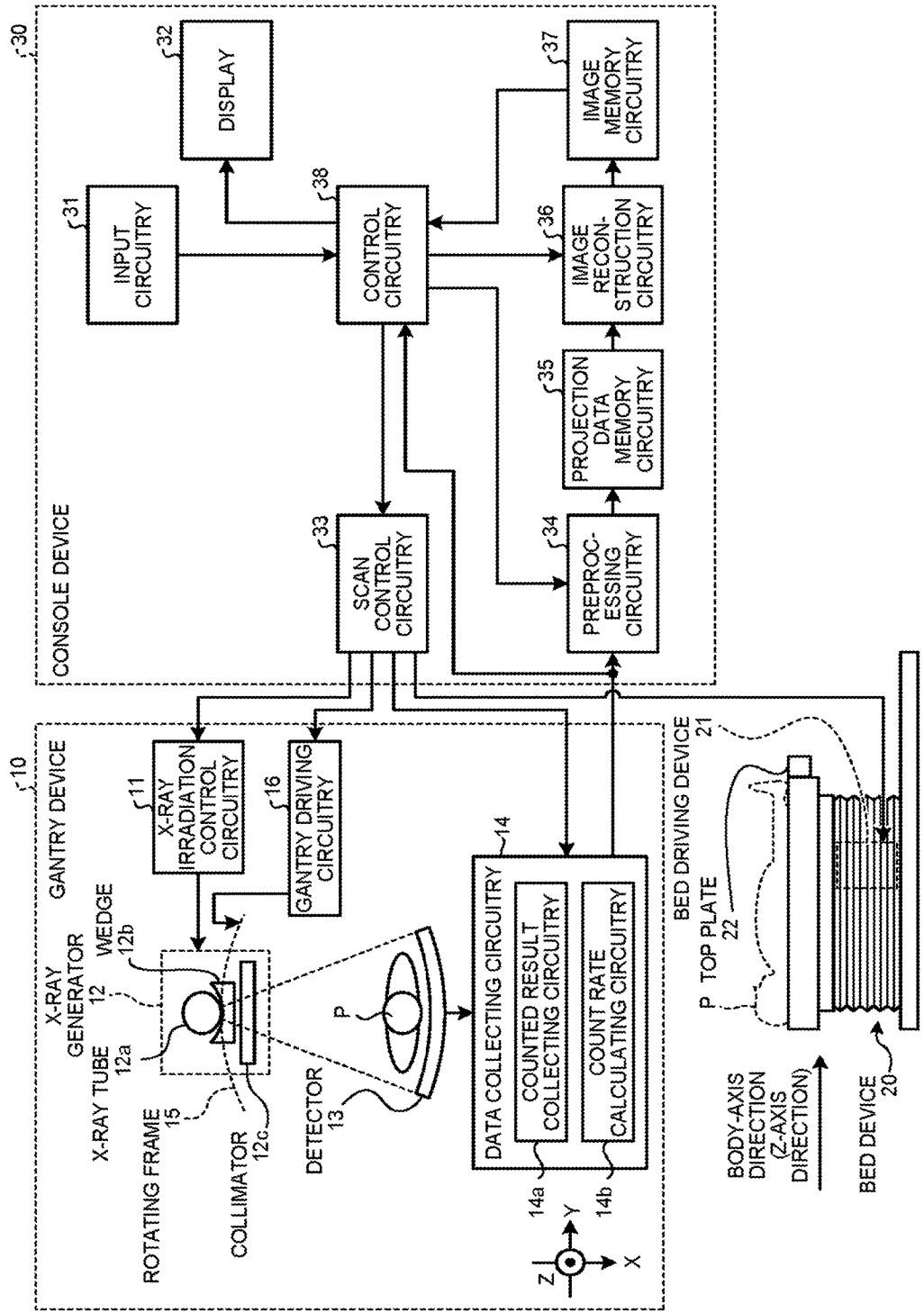
FIG. 2 is a block diagram of a configuration example of an X-ray CT apparatus according to a present embodiment.

Therefore, the X-ray CT apparatus according to the present embodiment is configured as follows in order to reconstruct a high quality image using the photon counting type detector. FIG. 2 is a block diagram of a configuration example of the X-ray CT apparatus according to the present embodiment. As illustrated in FIG. 2, the X-ray CT apparatus according to the present embodiment includes a gantry device 10, a bed device 20, and a console device 30.

The gantry device 10 is a device that irradiates a subject P with X-rays and collects results of counting X-rays having passed through the subject P, and includes X-ray irradiation control circuitry 11, an X-ray generator 12, a detector 13, data collecting circuitry 14, a rotating frame 15, and gantry driving circuitry 16.

The rotating frame 15 is an annular frame that supports the X-ray generator 12 and the detector 13 so as to face each other across the subject P, and that is rotated at a high speed by the gantry driving circuitry 16, explained later, on a circular path around the subject P.

The X-ray generator 12 is a device that generates X-rays and irradiates the subject P with generated X-rays, and includes an X-ray tube 12a, a wedge 12b, and a collimator 12c.

The X-ray tube 12a is a vacuum tube that irradiates the subject P with an X-ray beam by a high voltage supplied from the X-ray irradiation control circuitry 11, explained later, and irradiates the subject P with the X-ray beam in association with a rotation of the rotating frame 15. The X-ray tube 12a generates an X-ray beam that spreads with a fan angle and a cone angle.

The wedge 12b is an X-ray filter for adjusting an X-ray dose of the X-ray exposed from the X-ray tube 12a. For example, the wedge 12b is a filter made of aluminum. The wedge 12b is also called a "bowtie filter".

The collimator 12c is a slit for narrowing an irradiation range of the X-ray in which the X-ray dose is adjusted by the wedge 12b under the control of the X-ray irradiation control circuitry 11 explained later.

The X-ray irradiation control circuitry 11 is a device, as a high voltage generator, that supplies a high voltage to the X-ray tube 12a. The X-ray tube 12a generates X-rays using the high voltage supplied from the X-ray irradiation control circuitry 11. The X-ray irradiation control circuitry 11 adjusts the X-ray dose to be emitted to the subject P by adjusting a tube voltage and a tube current supplied to the X-ray tube 12a. The X-ray irradiation control circuitry 11 also adjusts the irradiation range of the X-ray (fan angle and cone angle) by adjusting the degree of aperture of the collimator 12c.

The gantry driving circuitry 16 rotationally drives the rotating frame 15 to thereby turn the X-ray generator 12 and the detector 13 on the circular path around the subject P.

The detector 13 is the photon counting type detector, and includes a plurality of detection elements each of which outputs a detection signal according to an incidence of an X-ray photon. Specifically, the detector 13 includes the detection elements each of which outputs a signal (detection signal) capable of measuring an energy value of an X-ray photon each time the X-ray photon enters. The photon counting type detector is roughly divided into a direct conversion type detector and an indirect conversion type detector. The direct conversion type detector is formed with a semiconductor that directly converts an incident X-ray photon into an electric signal. For example, a cadmium telluride (CdTe) semiconductor and a cadmium zinc telluride (CZT) semiconductor are used in the direct conversion type detector. The direct conversion type detector has a plurality of electrodes arranged on the opposite side of an X-ray photon incident surface of a semiconductor block in order to extract a signal. Thereby the semiconductor block of the direct conversion type detector is divided into a plurality of detection elements.

The indirect conversion type detector is formed by coupling a scintillator to, for example, a SiPM (Silicon Photomultiplier). In the indirect conversion type detector, the scintillator is divided into a plurality of sections using reflecting materials and is thereby divided into a plurality of detection elements. In the indirect conversion type detector, the scintillator converts the incident X-ray photon into scintillator light and an optical sensor such as SiPM converts the scintillator light into an electric signal.

The detector 13 according to the present embodiment includes a plurality of detection elements including a plurality of types of detection elements with different response characteristics to an X-ray dose. The types of detection elements with different response characteristics are arranged in a spatially mixed manner. For example, the detector 13 has detection elements with high response characteristics and detection elements with low response characteristics, which are arranged in a spatially mixed manner. Moreover, for example, the detection elements with high response characteristics and the detection elements with low response characteristics are alternately arranged. The detection element with low response characteristic is provided with, for example, a filter that reduces the number of incident X-ray photons. The detector 13 then outputs a detection signal (response waveform) in response to an incidence of an X-ray photon to each of the detection elements. "Response characteristic to an X-ray dose" mentioned here means "count rate characteristic to an X-ray dose". In other words, the detector 13 according to the present embodiment includes "a plurality of types of detection elements in which the number of signal outputs per unit time (the number of response waveforms per unit time) is different from each other even if the same amount of X-ray dose enters".

A case in which the detector 13 includes two types of detection elements whose count rate characteristics are different from each other (high sensitive element and low sensitive element) will be explained below. However, the present embodiment is applicable to even a case in which the detector 13 includes three or more types of detection elements whose count rate characteristics are different from one another. FIG. 3A, FIG. 3B, FIG. 4A, FIG. 4B, FIG. 5, and FIG. 6 are diagrams for explaining examples of the detector according to the present embodiment.

Figure 3A:
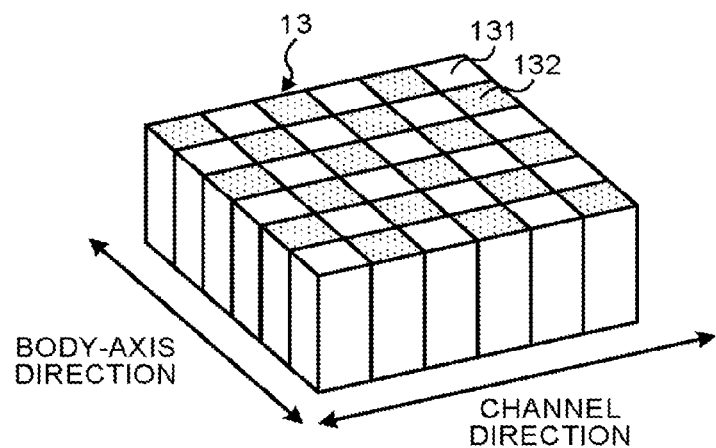
FIG. 3A, FIG. 3B, FIG. 4A and FIG. 4B are diagrams for explaining an example of a detector according to the present embodiment.
Figure 3B:
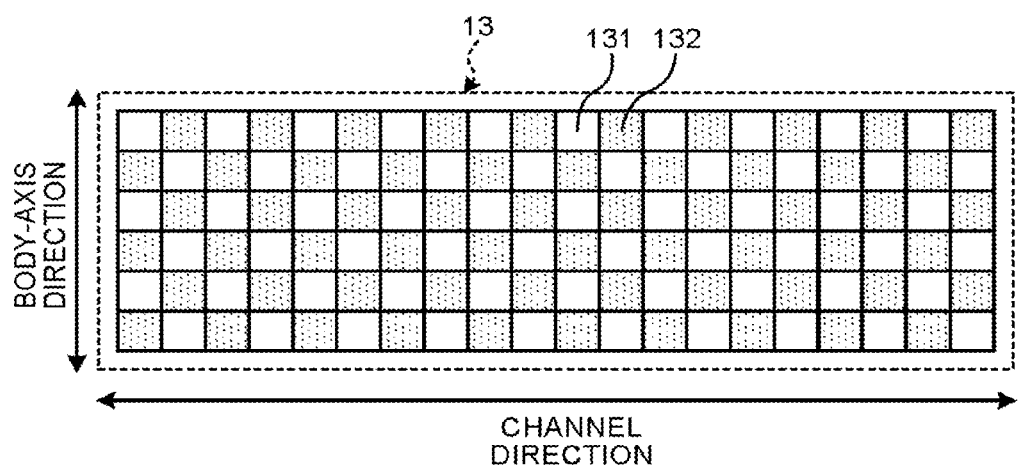

FIG. 3A is a perspective view of the detector 13 including a plurality of high sensitive elements 131 and a plurality of low sensitive elements 132, and FIG. 3B is a front view of the detector 13 illustrated in FIG. 3A when viewed from the X-ray photon incident surface. The detector 13 illustrated in FIG. 3A and FIG. 3B is a plane detector in which the high sensitive elements 131 and the low sensitive elements 132 are arranged in an alternately mixed manner, two-dimensionally in a channel direction and in a body-axis direction.

Figure 4A:
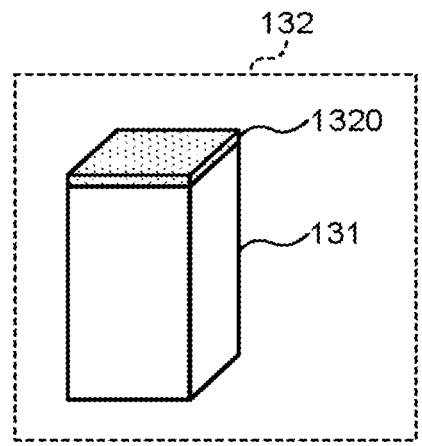
Figure 4B:
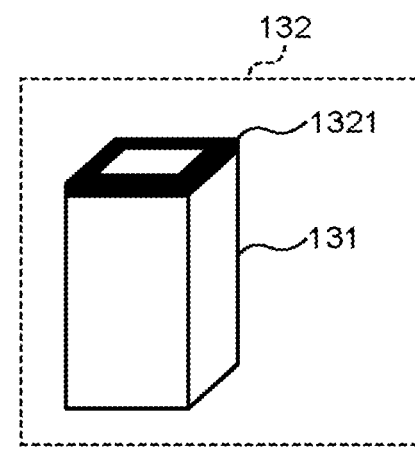

Even if the detector 13 as the direct conversion type detector is used, or even if the detector 13 as the indirect conversion type detector is used, the low sensitive element 132 can be made using a method illustrated in FIG. 4A and FIG. 4B. In the method illustrated in FIG. 4A, a sheet metal 1320 made of aluminum or zinc is provided on the X-ray photon incident surface of the high sensitive element 131 at a location that is desired to be low sensitivity among the two-dimensionally arranged high sensitive elements 131. In the method illustrated in FIG. 4A, the number of incident X-ray photons is restricted by the sheet metal 1320, so that part of the high sensitive elements 131 can function as the low sensitive elements 132.

In the method illustrated in FIG. 4B, an opening metal plate 1321, in which an opening is provided in a central portion of a metal plate capable of sufficiently blocking the X-rays, on the X-ray photon incident surface of the high sensitive element 131 at a location that is desired to be low sensitivity among the two-dimensionally arranged high sensitive elements 131. In the method illustrated in FIG. 4B, the number of incident X-ray photons can be restricted by the opening metal plate 1321, so that part of the high sensitive elements 131 can function as the low sensitive elements 132.

When the detector 13 as the indirect conversion type detector is used, the high sensitive elements 131 and the low sensitive elements 132 can be made by using scintillator materials with different light-emitting properties. For example, the scintillator of the high sensitive element 131 is made of LYSO (Lutetium Yttrium Oxyorthosilicate) or LGSO (Lutetium Gadelinium Oxyorthosilicate) with a high light-emitting property. For example, the scintillator of the low sensitive element 132 is made of ZnO (Zinc Oxide) with a low light-emitting property. By using the scintillator with the low light-emitting property, the number of photons reaching the optical sensor can be limited. Alternatively, when the detector 13 as the indirect conversion type detector is to be used, the high sensitive element 131 may be made by using a high density scintillator material and the low sensitive element 132 may be made by using a low density scintillator material even if the scintillators have the same material as each other. Alternatively, when the detector 13 as the indirect conversion type detector is to be used, the high sensitive element 131 may be made by using a thick scintillator and the low sensitive element 132 may be made by using a thin scintillator even if the scintillators have the same material as each other.

In the case of the direct conversion type detector, the detector 13 may be made so as to provide semiconductors having different count rate characteristics in a mixed manner and to arrange the high sensitive elements 131 and low sensitive elements 132 in a mixed manner.

Figure 5:
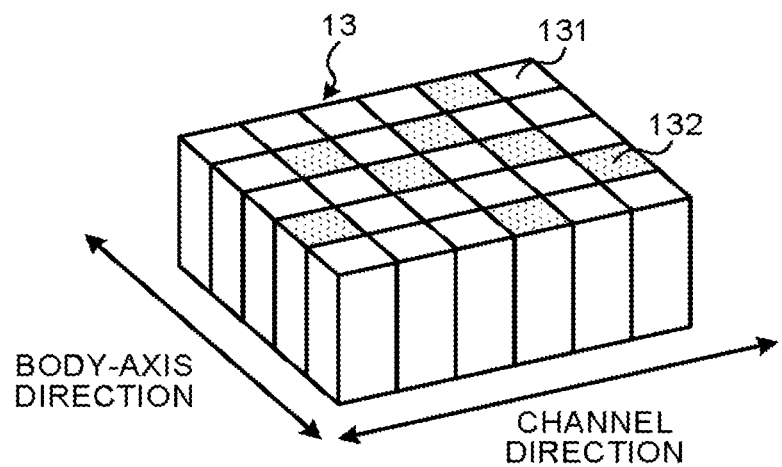
FIG. 5 and FIG. 6 are diagrams for explaining an example of the detector according to the present embodiment.

As illustrated in FIG. 3A and FIG. 3B, the detector 13 is not limited to the case in which the high sensitive elements 131 and the low sensitive elements 132 are arranged in a regularly alternating manner, two-dimensionally in the channel direction and in the body-axis direction. For example, as illustrated in FIG. 5, the detector 13 may be applied to a case in which the high sensitive elements 131 and the low sensitive elements 132 are randomly arranged, two-dimensionally in the channel direction and in the body-axis direction.

Figure 6:
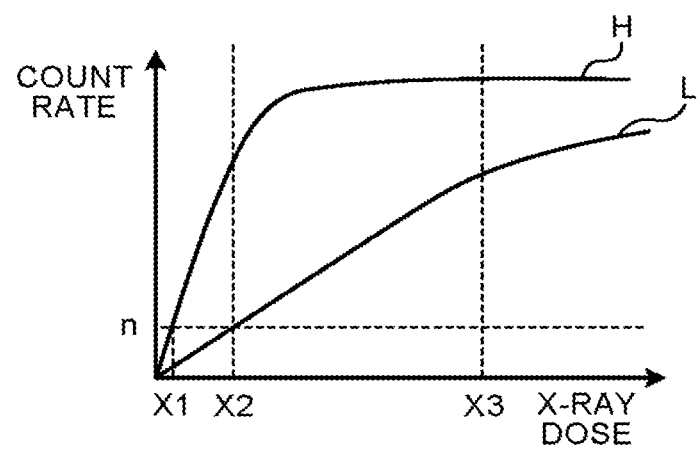

As explained above, by configuring the detector 13 by combining the detection elements (high sensitive elements 131 and the low sensitive elements 132) having different properties related to the count rate, it is possible to obtain signal output with a wide dynamic range with respect to the X-ray dose. A curve H illustrated in FIG. 6 represents response characteristic of the count rate with respect to the X-ray dose of the high sensitive element 131. A curve L illustrated in FIG. 6 represents response characteristic of the count rate with respect to the X-ray dose of the low sensitive element 132. Moreover, "n" illustrated in FIG. 6 represents a count rate corresponding to noise.

When comparing the curve H and the curve L illustrated in FIG. 6, an X-ray dose (X1) which is a count rate of a noise level in the high sensitive element 131 is smaller than an X-ray dose (X2) which is a count rate of a noise level in the low sensitive element 132. The curve H illustrated in FIG. 6 represents that counting loss of the number of photons occurs in the high sensitive elements 131 caused by the pile up when the X-ray dose exceeds X2. The curve L illustrated in FIG. 6 represents that counting loss of the number of photons occurs in the low sensitive element 132 caused by the pile up when the X-ray dose exceeds X3.

The curve H illustrated in FIG. 6 represents that, for example, the count rate characteristic of the high sensitive element 131 is approximately linear in a range of "from X1 to X2". The curve L illustrated in FIG. 6 represents that, for example, the count rate characteristic of the low sensitive element 132 is approximately linear in a range of "from X2 to X3".

The dynamic range with respect to the X-ray dose of the detector 13 including only the high sensitive elements 131 is the range of "from X1 to X2". The dynamic range with respect to the X-ray dose of the detector 13 including only the low sensitive elements 132 is the range of "from X2 to X3".

On the other hand, in the present embodiment, because the detector 13 is provided with the high sensitive elements 131 and the low sensitive elements 132, the dynamic range with respect to the X-ray dose of the detector 13 becomes wider as a range of "from X1 to X3". In other words, in the present embodiment, it is possible to manufacture the detector 13, at a low cost, which is the photon counting type detector capable of reducing the occurrence of the pile up, by being formed with a plurality of types of detection elements with different count rate characteristics.

Returning to FIG. 2, the data collecting circuitry 14 collects various types of information from the output signal of the detector 13. As illustrated in FIG. 2, the data collecting circuitry 14 according to the present embodiment includes counted result collecting circuitry 14a and count rate calculating circuitry 14b.

Specifically, the counted result collecting circuitry 14a collects a counted result obtained by counting X-ray photons from the signal (detection signal) output from each of the detection elements constituting the detector 13. The counted result collecting circuitry 14a transmits the collected counted results to the console device 30.

First of all, the counted result collecting circuitry 14a counts the number of X-ray photons by discriminating the signals (detection signals) output of each of the detection elements of the detector 13. The counted result collecting circuitry 14a collects an incident position (detection position) of a counted X-ray photon and an energy value of the X-ray photon as a counted result in each phase of the X-ray tube 12a (tube phase, view). The counted result collecting circuitry 14a determines, for example, the position of the detection element that outputs the electric signal used for counting as an incident position. The data collecting circuitry 14 and the processor of the console device 30, explained later, can determine whether the detection element that outputs the electric signal used for counting is the high sensitive element 131 or the low sensitive element 132 based on the incident position.

For example, the counted result collecting circuitry 14a calculates a wave height of the electric signal and calculates an energy value from the wave height and a system-specific response function. The response function is a function previously calculated from physical properties of the detection element, and is a function for calculating an energy value from the wave height. The counted result collecting circuitry 14a according to the present embodiment stores the response function of the high sensitive element 131 and the response function of the low sensitive element 132.

The counted result becomes information, for example, in a tube phase "α1", such that a count value of a photon having energy "E1" is "N1" and a count value of a photon having energy "E2" is "N2" in the high sensitive element 131 of an incident position "P11". Moreover, the counted result becomes information, for example, in the tube phase "α1", such that a count value of the photon having the energy "E1" is "N1'" and a count value of the photon having the energy "E2" is "N2'" in the low sensitive element 132 of an incident position "P12". The counted result may be a count value per unit time (count rate) instead of the count value.

The energy "E1" in the counted result may be set to, for example, an energy discrimination area "E1 to E2". In this case, the counted result becomes information, for example, in the tube phase "α1", such that a count value of a photon having the energy discrimination area "E1 to E2" is "NN1" in the high sensitive element 131 of the incident position "P11". Moreover, in this case, the counted result becomes information, for example, in the tube phase "α1", such that a count value of the photon having the energy discrimination areas "E1 to E2" is "NN1'" in the low sensitive element 132 of the incident position "P12". The energy discrimination area is an area where the counted result collecting circuitry 14a discriminates and distributes the value of energy to a predetermined granularity. A threshold for setting the energy discrimination area is set by, for example, control circuitry 38 explained later. The counted result may be a count value per unit (count rate) time instead of the count value.

The count rate calculating circuitry 14b calculates a count rate from the signal (detection signal) output by each of the detection elements. For example, the count rate calculating circuitry 14b according to the present embodiment calculates a count rate from the signals output by a detection element group of a type in which the response characteristic is the highest among the types of detection elements. In the present embodiment, the count rate calculating circuitry 14b calculates a count rate from the signals output by the high sensitive elements 131. The count rate calculating circuitry 14b then transmits the calculated count rate to the console device 30.

At least one of the data collecting circuitry 14 and the console device 30 (e.g., control circuitry 38, explained later) includes memory circuitry (not illustrated), and the memory circuitry stores respective response characteristics of the detection elements. The memory circuitry stores, for example, an LUT (Look Up Table) associated with the response characteristic of the detection element for each position of the detection element. The data collecting circuitry 14 or the console device 30 refers to, for example, the LUT, and can determine whether the detection element that outputs the detection signal used for counting is the high sensitive element 131 or the low sensitive element 132.

The count rate calculated by the count rate calculating circuitry 14b is used as an index for determining an image reconstruction method performed by image reconstruction circuitry 36 explained later. Count rate calculation processing performed by the count rate calculating circuitry 14b will be explained in detail later. The present embodiment may be a case in which the count rate calculating circuitry 14b calculates a count rate from the detection signals output by the low sensitive elements 132 and transmits the calculated count rate to the console device 30. This will be also explained later.

The bed device 20 is a device for placing the subject P, and includes a top plate 22 and a bed driving device 21. The top plate 22 is a plate on which the subject P is placed, and the bed driving device 21 moves the top plate 22 in a Z-axis direction and moves the subject P into the rotating frame 15.

In the examination by the X-ray CT apparatus, normally, by moving the top plate 22 while the X-rays are emitted from the X-ray tube 12a in a state of fixing the rotating frame 15, a scanogram is imaged in such a manner that the whole body of the subject P is scanned along the body-axis direction. In the imaging of the scanogram, the dose of the X-rays emitted from the X-ray tube 12a is adjusted to a dose to such an extent that a pile up will not occur in the detector 13.

An operator referring to the scanogram of the subject P plans an X-ray CT imaging plan. Based on this, for example, the gantry device 10 performs a helical scan to spirally scan the subject P by rotating the rotating frame 15 while moving the top plate 22. Alternatively, the gantry device 10 performs a conventional scan to scan the subject P on the circular path by rotating the rotating frame 15 while fixing the position of the subject P after the movement of the top plate 22. Alternatively, the gantry device 10 performs a step-and-shoot method of moving the position of the top plate 22 at a predetermined interval and performing the conventional scan in a plurality of scan areas.

The console device 30 is a device that receives an operation of the X-ray CT apparatus from the operator and reconstructs the X-ray CT image data using the counted results collected by the gantry device 10. As illustrated in FIG. 2, the console device 30 includes input circuitry 31, a display 32, scan control circuitry 33, preprocessing circuitry 34, projection data memory circuitry 35, the image reconstruction circuitry 36, image memory circuitry 37, and the control circuitry 38.

The input circuitry 31 includes a mouse, a keyboard, and the like used for input of various instructions and various settings made by the operator of the X-ray CT apparatus, and transmits information for an instruction and setting received from the operator to the control circuitry 38. For example, the input circuitry 31 receives reconstruction conditions for reconstruction of X-ray CT image data and image processing conditions for X-ray CT image data from the operator.

The display 32 is a monitor referred to by the operator, and, under the control of the control circuitry 38, displays the X-ray CT image data to the operator or displays a GUI (Graphical User Interface) for receiving various instructions and various settings or so from the operator via the input circuitry 31.

The scan control circuitry 33 controls, under the control of the control circuitry 38, the operations of the X-ray irradiation control circuitry 11, the gantry driving circuitry 16, the data collecting circuitry 14, and the bed driving device 21, to thereby control collection processing of the counted results in the gantry device 10.

The preprocessing circuitry 34 generates projection data by performing correction processing such as logarithmic conversion processing, offset correction, sensitivity correction, and beam hardening correction on the counted results transmitted from the counted result collecting circuitry 14a. The preprocessing circuitry 34 according to the present embodiment may perform, as the sensitivity correction, processing of correcting the counted result of the high sensitive element 131 and the counted result of the low sensitive element 132 to the counted results of the same level, from the count rate characteristic of the high sensitive element 131 and the count rate characteristic of the low sensitive element 132.

The present embodiment may be configured to dispose a reference detector for measuring radiation quality of X-rays (energy value) emitted from the X-ray tube 12a, at an end of the detector 13 or an area near the wedge 12b. In this case, the preprocessing circuitry 34 receives an energy value of X-rays emitted from the X-ray tube 12a and receives an energy value of X-rays not passing through the subject P, from the reference detector. The preprocessing circuitry 34 receives an energy value in each tube phase. The preprocessing circuitry 34 then corrects each of projection data in a plurality of tube phases using the energy value of each tube phase.

The projection data memory circuitry 35 stores projection data generated by the preprocessing circuitry 34. That is, the projection data memory circuitry 35 stores projection data (corrected counted result) for generating a scanogram and projection data (corrected counted result) for reconstructing X-ray CT image data. Hereinafter, the projection data may be described as a counted result.

The image reconstruction circuitry 36 reconstructs X-ray CT image data by using the projection data (projection data for reconstructing X-ray CT images) stored in the projection data memory circuitry 35. There are various methods as the reconstruction method which includes, for example, back projection processing. The back projection processing includes, for example, back projection processing using FBP (Filtered Back Projection) method. As the reconstruction method, successive approximation may be used. The image reconstruction circuitry 36 generates image data by performing various types of image processing on the X-ray CT image data. The image reconstruction circuitry 36 stores the reconstructed X-ray CT image data and the image data generated through the various types of image processing in the image memory circuitry 37.

The projection data generated from the counted results obtained through the photon counting CT includes information for energy of X-rays attenuated by passing through the subject P. The image reconstruction circuitry 36 can reconstruct, for example, X-ray CT image data for a specific energy component. The image reconstruction circuitry 36 can also reconstruct, for example, X-ray CT image data for each of a plurality of energy components.

The image reconstruction circuitry 36 generates a scanogram from the projection data for generation of scanogram stored in the projection data memory circuitry 35, and stores the generated scanogram in the image memory circuitry 37.

The image reconstruction circuitry 36 according to the present embodiment reconstructs the X-ray CT image data based on the count rate calculated by the count rate calculating circuitry 14b. The image reconstruction processing performed by the image reconstruction circuitry 36 will be explained in detail later.

The control circuitry 38 performs the overall control of the X-ray CT apparatus by controlling the operations of the gantry device 10, the bed device 20, and the console device 30. Specifically, the control circuitry 38 controls the scan control circuitry 33 to thereby control the collection processing of counted results in the gantry device 10. The control circuitry 38 also controls the preprocessing circuitry 34 and the image reconstruction circuitry 36 to thereby control the image processing in the console device 30. Moreover, the control circuitry 38 controls the scanogram and the X-ray CT image data stored in the image memory circuitry 37 so as to be displayed on the display 32.

The overall configuration of the X-ray CT apparatus according to the present embodiment has been explained as above. Based on the configuration, the X-ray CT apparatus according to the present embodiment reconstructs the X-ray CT image data using the counted results collected by the detector 13 with a wide dynamic range of the count rate characteristics.

As explained above, the count rate calculating circuitry 14b according to the present embodiment calculates, as an example, a count rate from the signals output by the high sensitive elements 131. Specifically, the count rate calculating circuitry 14b calculates a count rate from the signals output by the high sensitive elements 131 included in an interest region set in the detector 13. For example, the operator of the X-ray CT apparatus refers to the scanograms imaged respectively in the tube phases to determine an imaging cross section. The operator then sets a range including the subject P in each of the scanograms in the determined imaging cross section.

The control circuitry 38 estimates an outline of the subject P in the imaging cross section from the range set by the operator in each of the scanograms. Then, the control circuitry 38 determines, as the interest region, a region of the detector 13 which X-rays having passed through the subject P commonly in the respective tube phases are quite likely to enter, from the estimated outline. The control circuitry 38 or the operator may estimate the outline of the subject P by using the X-ray CT image data obtained by preliminarily imaging the imaging cross section through X-ray irradiation of low dose and being reconstructed.

Alternatively, the interest region may be, for example, previously set at the center portion of the detector 13. The present embodiment may also be configured that a plurality of interest regions are set according to weight and height and that the control circuitry 38 or the operator sets an interest region corresponding to the weight and height of the subject P.

The control circuitry 38 transmits the position information of the set interest region or the position information of the high sensitive element 131 included in the set interest region to the count rate calculating circuitry 14b through the scan control circuitry 33. The count rate calculating circuitry 14b calculates count rates from the signals output by the respective high sensitive elements 131 included in the interest region during imaging of the X-ray CT image data. For example, the count rate calculating circuitry 14b calculates respective count rates of the high sensitive elements 131 in the tube phases. Then, for example, the count rate calculating circuitry 14b calculates statistics of a plurality of count rates calculated while the rotating frame 15 is making one rotation, and transmits the calculated statistics to the control circuitry 38.

The statistics is, for example, a maximum value, an average, and a median of the count rates calculated while the rotating frame 15 is making one rotation. Alternatively, the statistics is, for example, an n-th (e.g., third) largest value among the count rates calculated while the rotating frame 15 is making one rotation. The type of the statistics may be set initially or may be set by the operator upon imaging. The count rate calculating circuitry 14b calculates the count rate calculated through statistical processing for each one rotation of the rotating frame 15 i.e. each time a projection data group for one frame is collected. In the present embodiment, the control circuitry 38 may calculate the statistics. In the present embodiment, the control circuitry 38 may calculate a count rate corresponding to the projection data group for one frame using the count rates of all the detection elements calculated by the count rate calculating circuitry 14b.

The image reconstruction circuitry 36 according to the present embodiment reconstructs the X-ray CT image data using the counted result obtained from the detection element with the response characteristic selected according to the count rate, among the counted results obtained from the detection elements. The selection of the response characteristic according to the count rate is performed by, for example, the control circuitry 38. In other words, the control circuitry 38 selects a detection element based on the count rate and the respective response characteristics of the detection elements. The image reconstruction circuitry 36 reconstructs the X-ray CT image data using the counted result obtained from the detection element selected by the control circuitry 38. Specifically, the control circuitry 38 selects a detection element with the response characteristic according to the count rate. The control circuitry 38 controls the image reconstruction circuitry 36 so as to perform reconstruction processing using the counted result obtained from the detection element with the response characteristic selected according to the count rate among the counted results collected by the counted result collecting circuitry 14a. The image reconstruction circuitry 36 according to the present embodiment reconstructs the X-ray CT image data using the counted results of the detection element group of which response characteristic is equal to or smaller than a predetermined value when the count rate is equal to or larger than a predetermined threshold, based on an instruction of the control circuitry 38. Specifically, the image reconstruction circuitry 36 according to the present embodiment reconstructs, when the count rate is equal to or larger than the predetermined threshold, the X-ray CT image data using the counted results of the detection element group of a type other than the type with the highest response characteristic. In the present embodiment, when the count rate is equal to or larger than the predetermined threshold, the image reconstruction circuitry 36 reconstructs the X-ray CT image data using the counted results (projection data) of the low sensitive elements 132.

For example, the predetermined threshold is set to the count rate at X-ray dose "X2" on the curve H illustrated in FIG. 6. In other words, when the count rate is a high count rate equal to or larger than the threshold, it is determined that an output is saturated in any one of the high sensitive elements 131 and that a projection data group in which a pile up is quite likely to occur is collected. The determination as to whether a projection data group, in which a pile up is quite likely to occur in any one of the high sensitive elements 131, is collected is performed by the control circuitry 38. As illustrated in the curve L of FIG. 6, in the case of the X-ray dose larger than the X-ray dose "X2", the response characteristic of the low sensitive element 132 is approximately linear.

As explained above, in the present embodiment, the count rate calculating circuitry 14b may calculate a count rate from the signals output by the low sensitive elements 132. In this case, the count rate calculating circuitry 14b calculates "statistics of count rates" based on the signals output by the low sensitive elements 132, for example, each time a projection data group for one frame is collected, and transmits calculated value to the control circuitry 38. The predetermined threshold in this case is set to, for example, the count rate at X-ray dose "X2" on the curve L illustrated in FIG. 6. By comparing the threshold and the statistics of the count rates obtained from the low sensitive elements 132, the control circuitry 38 can determine whether a projection data group in which a pile up is quite likely to occur in any one of the high sensitive elements 131 is collected.

Figure 7:
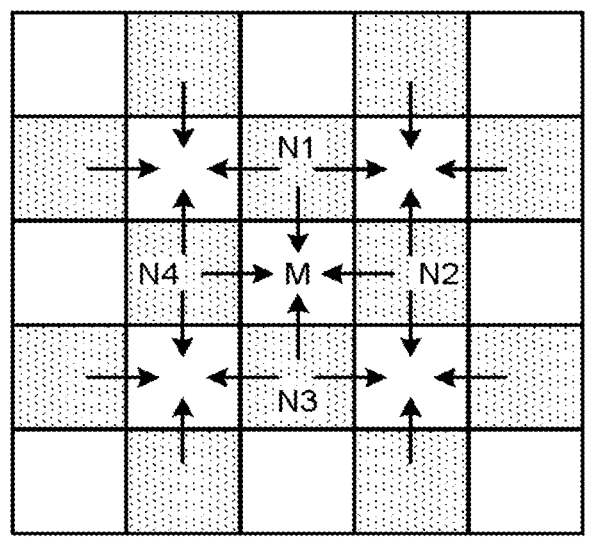
FIG. 7 is a diagram of an example of processing performed by image reconstruction circuitry at high count rate.

FIG. 7 is a diagram of an example of the processing performed by the image reconstruction circuitry at high count rate. The image reconstruction circuitry 36, which an instruction to perform reconstruction processing at high count rate is notified from the control circuitry 38, reads a projection data group for one frame corresponding to the positions of the low sensitive elements 132 from the projection data groups for one frame stored in the projection data memory circuitry 35. The read processing of the projection data group can be performed by the instruction from the control circuitry 38 that refers to the LUT. However, the projection data in each tube phase forming the projection data group becomes projection data with the lack of position information of the high sensitive element 131.

Therefore, for example, as illustrated in FIG. 7, the image reconstruction circuitry 36 interpolates the projection data (counted result) for the position of the high sensitive element 131 (see "M" in FIG. 7) using the projection data (counted results) for the positions ("N1 to N4" in FIG. 7) of four surrounding low sensitive elements 132. The image reconstruction circuitry 36 performs the interpolation processing illustrated in FIG. 7 on the missing projection data in all the tube phases, to thereby generate a complete projection data group for one frame and reconstruct the X-ray CT image.

Alternatively, the image reconstruction circuitry 36 uses, for example, a convex projection method to estimate a missing portion from the projection data with the lack of position information of the high sensitive element 131. The convex projection method is also called "POCS (Projection Onto Convex Sets) method", which is set-theoretic signal restoration that estimates a super-resolved image by sequentially solving individual simultaneous equations established between pixel values of the high sensitive elements and the low sensitive elements after satisfying a limiting condition that all the equations are convex set, and is applicable to the projection data.

The image reconstruction circuitry 36 generates complete projection data by, instead of performing interpolation processing, estimating the missing portion using the convex projection method from the projection data with the lack of the position information of the high sensitive element 131. The image reconstruction circuitry 36 performs the estimation processing on the missing projection data using the convex projection method in all the tube phases, to thereby generate a complete projection data group for one frame and reconstruct the X-ray CT image.

On the other hand, when the count rate is smaller than the predetermined threshold, the image reconstruction circuitry 36 reconstructs the X-ray CT image data using the counted results of the detection element group of a type in which the response characteristic becomes approximately linear at an X-ray dose smaller than the X-ray dose corresponding to the predetermined threshold. In the present embodiment, the image reconstruction circuitry 36 reconstructs the X-ray CT image data using the counted results (projection data) of the high sensitive elements 131 when the count rate is smaller than the predetermined threshold. As explained above, the predetermined threshold is set to the count rate at the X-ray dose "X2" on the curve H (or curve L) illustrated in FIG. 6. As illustrated in the curve H of FIG. 6, the response characteristics of the high sensitive element 131 is approximately linear at an X-ray dose smaller than the X-ray dose "X2".

Figure 8:
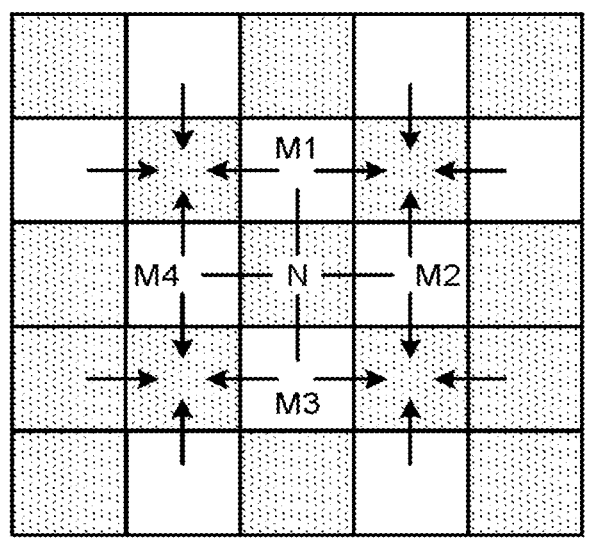
FIG. 8 is a diagram of an example of processing performed by the image reconstruction circuitry at low count rate.

FIG. 8 is a diagram of an example of the processing performed by the image reconstruction circuitry at low count rate. The image reconstruction circuitry 36, which an instruction to perform reconstruction processing at low count rate is notified from the control circuitry 38, reads a projection data group corresponding to the positions of the high sensitive elements 131 from the projection data groups for one frame stored in the projection data memory circuitry 35. The projection data in each tube phase forming the projection data group becomes projection data with the lack of position information of the low sensitive elements 132. The read processing of the projection data group can also be performed by the instruction from the control circuitry 38 that refers to the LUT.

For example, as illustrated in FIG. 8, the image reconstruction circuitry 36 interpolates the projection data (counted result) for the position (see "N" in FIG. 8) of the low sensitive element 132 using the projection data (counted results) for positions (see "M1 to M4" in FIG. 8) of four surrounding high sensitive elements 131. The image reconstruction circuitry 36 performs the interpolation processing illustrated in FIG. 8 on the missing projection data in all the tube phases, to thereby generate a complete projection data group for one frame and reconstruct the X-ray CT image data.

Alternatively, the image reconstruction circuitry 36 uses, for example, the convex projection method to estimate a missing portion from the projection data with the lack of position information of the low sensitive element 132, and generates complete projection data. The image reconstruction circuitry 36 performs the estimation processing on the missing projection data using the convex projection method in all the tube phases, to thereby generate the complete projection data group for one frame and reconstruct the X-ray CT image data.

When the count rate is smaller than the predetermined threshold, the image reconstruction circuitry 36 may reconstruct the X-ray CT image data using a counted result obtained by summing weighted counted results of a plurality of types of the detection elements. In the present embodiment, the image reconstruction circuitry 36 reconstructs the X-ray CT image data using a counted result obtained by summing weighted counted results of the high sensitive elements 131 and weighted counted results of the low sensitive elements 132. When the method is to be performed, in the preprocessing circuitry 34, it is preferable to perform the correction processing on the counted results using the reference detector and to perform the sensitivity correction processing of correcting the counted result corresponding to the position of the high sensitive element 131 and the counted result corresponding to the position of the low sensitive element 132 to the counted results of the same level.

Figure 9A:
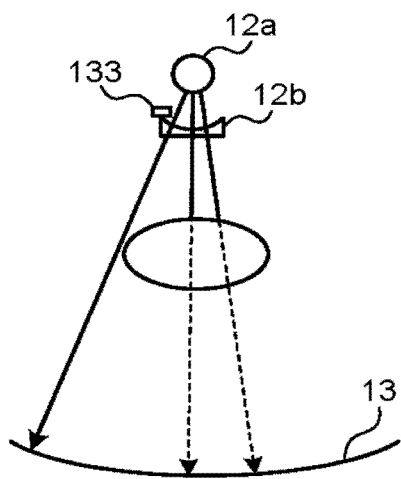
FIG. 9A and FIG. 9B are diagrams of another example of the processing performed by the image reconstruction circuitry at the low count rate.
Figure 9B:
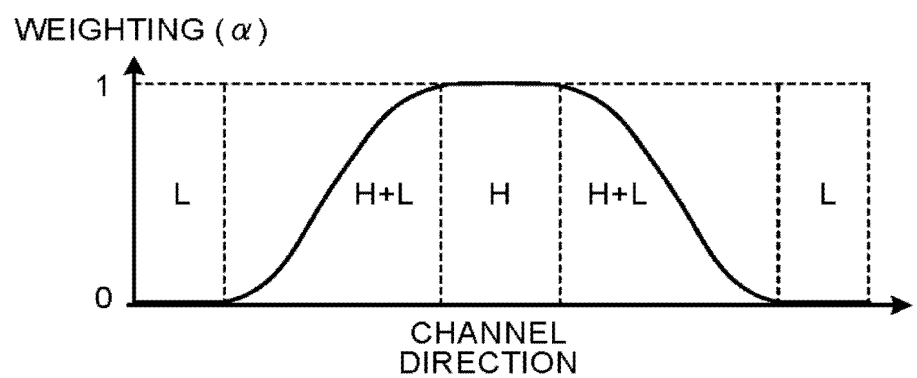

FIG. 9A and FIG. 9B are diagrams of another example of the processing performed by the image reconstruction circuitry at the low count rate. As illustrated in FIG. 9A, the dose of the X-ray photon generated by the X-ray tube 12a is adjusted by the wedge 12b, and the adjusted X-ray photon is incident on the detector 13. FIG. 9A also represents a reference detector 133 disposed between the X-ray tube 12a and the wedge 12b.

The X-ray photon emitted from the X-ray tube 12a is attenuated when passing through the subject P and is incident on the detector 13 as illustrated in FIG. 9A. On the other hand, when not passing through the subject P (i.e., when passing through only the air) as illustrated in FIG. 9A, the X-ray photon emitted from the X-ray tube 12a is incident on the detector 13 without being attenuated. The X-ray photon emitted from the X-ray tube 12a and passing through the subject P differs in the degree of attenuation depending on the thickness of the subject P through which the X-ray photon passes.

When performing the reconstruction processing using the summed counted result which is weighted at the low count rate, the control circuitry 38 or the operator uses the X-ray CT image data reconstructed by the scanogram of the subject P or by the preliminary imaging thereof to set a profile of weighting ($\alpha$, $0 \leq \alpha \leq 1$) as illustrated in FIG. 9B. FIG. 9B exemplifies a weighting profile in the channel direction. The control circuitry 38 or the operator sets a weighting profile also in the body-axis direction.

The position of "$\alpha=0$" in the profile illustrated in FIG. 9B represents a position where no subject P is present in the X-ray irradiation direction. Because a high dose X-ray photon which is not attenuated is incident on the position of "$\alpha=0$", it is preferable to use the counted result (L) of the low sensitive element 132. The position of "$\alpha=1$" in the profile illustrated in FIG. 9B represents a position where the thickness of the subject P in the X-ray irradiation direction is larger than a given value. Because a low dose X-ray photon with a large attenuance is incident on the position of "α=1", it is preferable to use the counted result (H) of the high sensitive element 131.

A position of "0<α<1" in the profile illustrated in FIG. 9B represents a position where the thickness of the subject P is smaller than the given value although the subject P is present in the X-ray irradiation direction. Because the attenuance is different depending on the thickness of the subject P at the position of "0<α<1", it is preferable to use the counted result (L) together with the counted result (H).

The image reconstruction circuitry 36 approximates the counted result of the high sensitive element 131 at the position of "α=0" through the interpolation processing using the counted results (L) of the low sensitive elements 132 (see FIG. 7). Alternatively, the image reconstruction circuitry 36 estimates the counted result of the high sensitive element 131 at the position of "α=0" using the convex projection method. The image reconstruction circuitry 36 approximates the counted result of the low sensitive element 132 at the position of "α=1" through the interpolation processing using the counted results (H) of the high sensitive elements 131 (see FIG. 8). Alternatively, the image reconstruction circuitry 36 estimates the counted result of the low sensitive element 132 at the position of "α=1" using the convex projection method.

The image reconstruction circuitry 36 calculates the counted result (projection data) of the high sensitive element 131 at a position of "0<α<1", for example, in the following manner. The counted result of the high sensitive element 131 at the position "M" illustrated in FIG. 7 is set to "CM", and the counted results of the low sensitive elements 132 at the positions "N1 to N4" illustrated in FIG. 7 are set to "CN1 to CN4" respectively. "CM, CN1, CN2, CN3, and CN4" are counted results obtained through the sensitivity correction processing. In this case, the image reconstruction circuitry 36 calculates the counted result of the position "M" using "α×CM+{(1−α)/4}×(CN1+CN2+CN3+CN4)".

The image reconstruction circuitry 36 calculates the counted result (projection data) of the low sensitive element 132 at a position of "0<α<1", for example, in the following manner. The counted result of the low sensitive element 132 at the position "N" illustrated in FIG. 8 is set to "CN", and the counted results of the high sensitive elements 131 at the positions "M1 to M4" illustrated in FIG. 8 are set to "CM1 to CM4" respectively. "CN, CM1, CM2, CM3, and CM4" are counted results obtained through the sensitivity correction processing. In this case, the image reconstruction circuitry 36 calculates the counted result of the position "N" using "(1−α)×CN+(α/4)×(CM1+CM2+CM3+CM4)".

Thus, the image reconstruction circuitry 36 generates the projection data group for one frame at the low count rate and reconstructs the X-ray CT image data. The weighting profile illustrated in FIG. 9B may be initially set for each body type of a patient. In this case, for example, the operator inputs information on the body type of the subject P, and the control circuitry 38 transfers the weighting profile corresponding to the input information to the image reconstruction circuitry 36.

The processing for the counted result may be performed by the preprocessing circuitry 34 or by the control circuitry 38. The processing may be performed on a plurality of imaging cross sections for generation of volume data.

Figure 10:
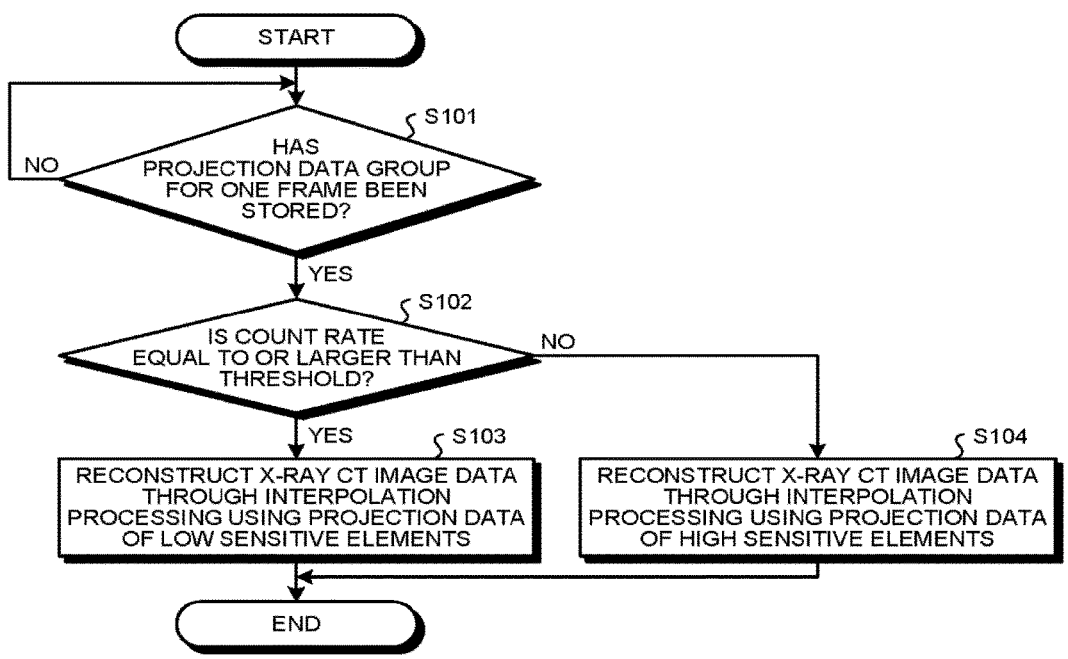
FIG. 10 is a flowchart for explaining an example of the processing of the X-ray CT apparatus according to the present embodiment.

An example of the processing performed by the X-ray CT apparatus according to the present embodiment will be explained next with reference to FIG. 10. FIG. 10 is a flowchart for explaining an example of the processing of the X-ray CT apparatus according to the present embodiment. The flowchart illustrated in FIG. 10 exemplifies the cases of performing the interpolation processing illustrated in FIG. 7 and FIG. 8.

As illustrated in FIG. 10, the control circuitry 38 of the X-ray CT apparatus according to the present embodiment determines whether the projection data group for one frame has been stored in the projection data memory circuitry 35 (Step S101). When the projection data group for one frame has not been stored therein (No at Step S101), the control circuitry 38 waits until the projection data group for one frame is stored therein.

Meanwhile, when the projection data group for one frame has been stored (Yes at Step S101), the control circuitry 38 determines whether the count rate of the high sensitive element 131 at the time of collecting the projection data group is equal to or larger than a threshold (Step S102). When the count rate is equal to or larger than the threshold (Yes at Step S102), the image reconstruction circuitry 36 generates the projection data group for one frame through the interpolation processing using the projection data of the low sensitive elements 132 based on the instruction of the control circuitry 38, reconstructs the X-ray CT image data (Step S103), and ends the processing.

Meanwhile, when the count rate is smaller than the threshold (No at Step S102), the image reconstruction circuitry 36 generates the projection data group for one frame through the interpolation processing using the projection data of the high sensitive elements 131 based on the instruction of the control circuitry 38, reconstructs the X-ray CT image data (Step S104), and ends the processing.

The X-ray CT image data reconstructed at Step S103 and Step S104 are displayed on, for example, the display 32. When CT imaging is performed along the time series, the flowchart of FIG. 10 is repeated.

As explained above, in the present embodiment, a photon counting type detector with a wide dynamic range can be manufactured at low cost using a plurality of types of detection elements with different response characteristics (count rate characteristics) with respect to the X-ray dose. In the present embodiment, by using the photon counting type detector, the X-ray CT image data is reconstructed.

In the present embodiment, in the case of the high count rate in which a pile up is quite likely to occur in the detection element with high response characteristic, the X-ray CT image data is reconstructed by using the counted results of the detection element group with low response characteristics. In the present embodiment, in the case of the low count rate, the X-ray CT image data is reconstructed by using the counted results of the detection element group with high response characteristics or using the counted result obtained by summing weighted counted results of all types of detection element group. Therefore, the present embodiment makes it possible to reconstruct a high quality image by using the photon counting type detector.

In the present embodiment, for example, when the detector 13 is manufactured by using three types of detection elements with different response characteristics (count rate characteristics) to the X-ray dose, the following reconstruction processing is performed. A detection element with highest count rate characteristic is referred to as a first detection element, a detection element with middle count rate characteristic is referred to as a second detection element, and a detection element with lowest count rate characteristic is referred to as a third detection element.

In the curve representing the count rate characteristic of the first detection element, a count rate corresponding to an X-ray dose "XA" in which the pile up occurs in the first detection element is referred to as "THA". In the curve representing the count rate characteristic of the second detection element, a count rate corresponding to an X-ray dose "XB" in which the pile up occurs in the second detection element is referred to as "THB". In the curve representing the count rate characteristic of the third detection element, a count rate corresponding to an X-ray dose "XC" in which the pile up occurs in the third detection element is referred to as "THC". The count rate characteristic of the first detection element represents an X-ray dose smaller than XA and is approximately linear, the count rate characteristic of the second detection element represents an X-ray dose from XA to XB and is approximately linear, and the count rate characteristic of the third detection element represents an X-ray dose from XB to XC and is approximately linear.

In this case, count rate calculation is performed using signals respectively output from a first detection element group, a second detection element group, and a third detection element group, which are included in the interest region set in the detector 13. For example, when the count rate (statistics) of the first detection element group is smaller than THA, the image reconstruction circuitry 36 reconstructs the X-ray CT image data by the interpolation processing using the counted result of the first detection element group or by the convex projection method. Alternatively, the image reconstruction circuitry 36 reconstructs the X-ray CT image data from the counted result obtained by summing, for example, the counted result of the first detection element group, the counted result of the second detection element group, and the counted result of the third detection element group, which are weighted.

When the count rate (statistics) of the first detection element group is equal to or larger than THA and the count rate (statistics) of the first detection element group is smaller than THB, the image reconstruction circuitry 36 reconstructs the X-ray CT image data by, for example, the interpolation processing using the counted result of the second detection element group or by the convex projection method. Alternatively, the image reconstruction circuitry 36 reconstructs the X-ray CT image data from the counted result obtained by summing, for example, the counted result of the second detection element group and the counted result of the third detection element group, which are weighted.

When the count rate (statistics) of the second detection element group is equal to or larger than THB and the count rate (statistics) of the third detection element group is smaller than THC, the image reconstruction circuitry 36 reconstructs the X-ray CT image data by, for example, the interpolation processing using the counted result of the third detection element group or by the convex projection method. This also makes it possible to reconstruct a high quality image using the photon counting type detector.

The present embodiment has explained the case in which the console device 30 that receives the counted results collected by the counted result collecting circuitry 14a selects the counted result used for reconstruction processing based on the count rate calculated by the count rate calculating circuitry 14b. However, the present embodiment may also be configured that the gantry device 10 selects the counted result used for the reconstruction processing based on the count rate and transmits the selected counted result to the console device 30. In this case, for example, the counted result collecting circuitry 14a receives the count rate calculated by the count rate calculating circuitry 14b. The counted result collecting circuitry 14a then selects the counted result obtained from the detection element with the response characteristic according to the count rate, and outputs the selected counted result to the console device 30 (image reconstruction circuitry 36). The selection processing of the counted result becomes possible by providing the LUT in the data collecting circuitry 14. In this modified example, a reconstruction processing method using the counted result selected by the data collecting circuitry 14 may be instructed by the data collecting circuitry 14 or may be instructed by the control circuitry 38. In this modified example, by selecting the counted result in the side of the gantry device 10, the data amount to be transmitted to the console device 30 can be reduced. The counted result collecting circuitry 14a performs a selection of the counted result substantially based on the instruction of the control circuitry 38.

The present embodiment has explained the case, as an example, in which the counted result for reconstruction is selected using the count rate calculated while the counted results for one frame are collected. However, the present embodiment may also be configured that the selection processing of the counted result for reconstruction is performed at a higher time resolution. For example, the count rate calculating circuitry 14b may calculate a count rate in each phase (in each tube phase, in each view) of the X-ray tube 12a that emits X-rays. In this case, the X-ray CT apparatus performs a selection of response characteristic according to the count rate (selection of the counted result according to the count rate) and a selection of a reconstruction processing method according to the count rate (selection of an interpolation method of projection data) by views. A position of a high count rate and a position of a low count rate in the X-ray photon incident surface of the detector 13 change in each view according to, for example, the body type of the subject P. In this modified example, because the count rate is calculated in each view and the reconstruction processing is controlled, a high quality image can be reliably reconstructed.

Furthermore, in the present embodiment, if the body shape of the subject P in FOV (Field of View) is approximately circular or if it does not matter whether it is such a rough selection that ignores the change in the body shape of the subject P in the FOV for each view, the following two modified examples are applicable. In a first modified example, the count rate calculating circuitry 14b calculates a count rate in an arbitrary phase of the X-ray tube that emits X-rays during imaging of the X-ray CT image data. Then, the control circuitry 38 performs a selection of response characteristic (selection of the counted result according to the count rate) and a selection of a reconstruction processing method according to the count rate (selection of an interpolation method of projection data) based on the count rate calculated in an arbitrary phase. For example, the count rate calculating circuitry 14b calculates a count rate in a first view immediately after the start of imaging, and notifies the control circuitry 38 of the calculated count rate.

Alternatively, in a second modified example, the count rate calculating circuitry 14b calculates a count rate during imaging of a scanogram. Then, the control circuitry 38 performs a selection of response characteristic (selection of the counted result according to the count rate) and a selection of a reconstruction processing method according to the count rate (selection of an interpolation method of projection data) based on the count rate calculated when the scanogram is imaged. For example, in the second modified example, the control circuitry 38 selects a detection element using the count rate calculated at the position including FOV in the scanogram.

As the medical image diagnostic apparatus using the photon counting type detector, a nuclear medical imaging apparatus is known, such as a Positron Emission CT apparatus (PET apparatus, PET: Positron Emission Computed Tomography) and a SPECT apparatus (SPECT: Single Photon Emission Computed Tomography). In the nuclear medical imaging apparatus also, when radiation photons (gamma ray photons) frequently enter the photon counting type detector, a pile up occurs, and the image quality of the PET image data and the SPECT image data is degraded.

The content described in the present embodiment can be applied to the medical image diagnostic apparatus which is the nuclear medical imaging apparatus. Each of the detection elements constituting the detector of the medical image diagnostic apparatus outputs a signal capable of measuring energy of a radiation photon according to an incidence of the radiation photon. The detector includes a plurality of detection elements including a plurality of types of detection elements with different response characteristics with respect to a radiation dose. The types of detection elements with different response characteristics are arranged in a spatially mixed manner. The medical image diagnostic apparatus uses the signals (detection signals) output by the respective detection elements that constitute the detector to collect the counted result obtained by counting radiation photons. Moreover, the medical image diagnostic apparatus calculates a count rate from the signals (detection signals) output by the detection elements that constitute the detector.

The medical image diagnostic apparatus selects a detection element based on the count rate and each response characteristic of the detection elements, and reconstructs medical image data by using the counted result obtained from the selected detection element. Specifically, the medical image diagnostic apparatus reconstructs medical image data by using the counted result obtained from the detection element with response characteristic selected based on the count rate among the counted results obtained from the detection elements. More specifically, when the count rate is equal to or larger than the predetermined threshold, the medical image diagnostic apparatus reconstructs the medical image data by using the counted result of the detection element group whose response characteristic is equal to or smaller than the predetermined value. More specifically, when the count rate is equal to or larger than the predetermined threshold, the medical image diagnostic apparatus reconstructs the medical image data by using the counted result of the detection element group of a type other than the type whose response characteristic is highest. The modified example is capable of reconstructing a high quality nuclear medical image using the photon counting type detector.

The components of the apparatuses or devices illustrated in the embodiment and the modified examples are functionally conceptual, and need not physically configured as illustrated. In other words, specific forms of distribution and integration of the apparatuses or devices are not limited to the illustrated ones, and whole of or part of the components can be functionally or physically distributed or integrated by arbitrary units based on various types of loads and use conditions. Moreover, the processing functions performed in the devices can be entirely or partially implemented by a CPU and by programs that are analyzed and executed by the CPU, or can be implemented as hardware by wired logic.

The reconstruction method using the photon counting type detector explained in the embodiment and the modified examples can be implemented by a computer such as a personal computer or a work station executing a preinstalled reconstruction program. The reconstruction program can be distributed through a network such as the Internet. Moreover, the reconstruction program can be executed by being recorded in a computer-readable recording medium such as hard disk, flexible disk (FD), CD-ROM, MO, and DVD and being read from the recording medium by the computer.

As explained above, according to the embodiment and the modified examples, it is possible to reconstruct a high quality image using the photon counting type detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modified examples as would fall within the scope and spirit of the inventions.

What is claimed is:

1. An X-ray CT apparatus comprising:
   a detector, including a plurality of detection elements including a plurality of types of detection elements with different response characteristics to an X-ray dose, and configured to output a detection signal according to an incidence of X-ray photons to each of the detection elements, the plurality of types of detection elements being arranged in the detector randomly, without forming a regularly-ordered pattern of the plurality of types of detection elements in the detector;
   counted result collecting circuitry configured to collect counted results obtained by counting the X-ray photons from detection signals output by the detection elements;
   count rate calculating circuitry configured to calculate a count rate from the detection signals output by the detection elements;
   control circuitry configured to select a detection element based on the count rate and respective response characteristics of the detection elements; and
   image reconstruction circuitry configured to reconstruct X-ray CT image data using the counted result obtained from the detection element selected by the control circuitry.

2. The X-ray CT apparatus according to claim 1, further comprising memory circuitry configured to store respective response characteristics of the detection elements.

3. The X-ray CT apparatus according to claim 1, wherein the image reconstruction circuitry is configured to reconstruct, when the count rate is equal to or larger than a predetermined threshold, X-ray CT image data using counted results of a detection element group whose response characteristic is equal to or smaller than a predetermined value.

4. The X-ray CT apparatus according to claim 3, wherein a filter that reduces number of incident X-ray photons is provided for one of the plurality of types of detecting elements.

5. The X-ray CT apparatus according to claim 3, wherein, when the count rate is smaller than the predetermined threshold, the image reconstruction circuitry is configured to reconstruct the X-ray CT image data by using counted results of one type out of the plurality of types of detecting elements, response characteristic of the one type of detecting elements being approximately linear at an X-ray dose smaller than an X-ray dose corresponding to the predetermined threshold.

6. The X-ray CT apparatus according to claim 3, wherein, when the count rate is smaller than the predetermined threshold, the image reconstruction circuitry is configured to reconstruct the X-ray CT image data by using a counted result obtained by summing weighted counted results of the plurality of types of detection elements.

7. The X-ray CT apparatus according to claim 1, wherein the count rate calculating circuitry is configured to calculate the count rate in each angle of an X-ray tube that emits X-rays.

8. The X-ray CT apparatus according to claim 1, wherein the count rate calculating circuitry is configured to calculate the count rate in any angle of an X-ray tube that emits X-rays during imaging of the X-ray CT image data.

9. The X-ray CT apparatus according to claim 1, wherein the count rate calculating circuitry is configured to calculate the count rate during imaging of a scanogram performed by the X-ray CT apparatus.

10. A medical image diagnostic apparatus comprising:
- a detector includes a plurality of detection elements including a plurality of types of detection elements with different response characteristics to an X-ray radiation dose, the plurality of types of detection elements being arranged in the detector randomly, without forming a regularly-ordered pattern of the plurality of types of detection elements in the detector, and configured to output a detection signal according to an incidence of X-ray radiation photons to each of the detection elements;
- counted result collecting circuitry configured to collect counted results obtained by counting the X-ray radiation photons from detection signals output by the detection elements;
- count rate calculating circuitry configured to calculate a count rate from the detection signals output by the detection elements;
- control circuitry configured to select a detection element based on the count rate and respective response characteristics of the detection elements; and
- image reconstruction circuitry configured to reconstruct medical image data using the counted result obtained from the detection element selected by the control circuitry.

* * * * *